US011166457B1

(12) United States Patent
Zou et al.

(10) Patent No.: US 11,166,457 B1
(45) Date of Patent: Nov. 9, 2021

(54) **ENVIRONMENTALLY RESPONSIVE *PAECILOMYCES LILACINUS* MICROBEAD AND PREPARATION METHOD THEREOF**

(71) Applicant: Jiangxi Huawei Technology Co., Ltd., Nanchang (CN)

(72) Inventors: Liqiang Zou, Nanchang (CN); Tong Wu, Nanchang (CN); Guizhong Chen, Nanchang (CN); Wei Liu, Nanchang (CN)

(73) Assignee: Jiangxi Huawei Technology Co., Ltd., Nanchang (CN)

( * ) Notice: Subject to any disclaimer, the term of this patent is extended or adjusted under 35 U.S.C. 154(b) by 0 days.

(21) Appl. No.: 17/133,640

(22) Filed: Dec. 24, 2020

(30) Foreign Application Priority Data

Sep. 27, 2020 (CN) ......................... 202011029908.7

(51) Int. Cl.
*A01N 25/28* (2006.01)
*C12N 1/14* (2006.01)
*B01J 13/14* (2006.01)
*A01N 25/30* (2006.01)
*A01N 65/00* (2009.01)

(52) U.S. Cl.
CPC ............. *A01N 25/28* (2013.01); *A01N 25/30* (2013.01); *A01N 65/00* (2013.01); *B01J 13/14* (2013.01); *C12N 1/14* (2013.01)

(58) Field of Classification Search
CPC ........ A01N 25/28; A01N 25/30; A01N 65/00; B01J 13/14; C12N 1/14
USPC .......................................................... 424/408
See application file for complete search history.

(56) References Cited

U.S. PATENT DOCUMENTS

2011/0027232 A1* 2/2011 Harman ................. A01N 63/20
424/93.4
2018/0289001 A1* 10/2018 Lalgudi .................. A01N 25/04

* cited by examiner

*Primary Examiner* — Ali Soroush
*Assistant Examiner* — Courtney A Brown
(74) *Attorney, Agent, or Firm* — Bayramoglu Law Offices LLC

(57) ABSTRACT

An environmentally responsive *Paecilomyces lilacinus* microbead and its preparation method and application are provided. The *Paecilomyces lilacinus* microbead includes a capsule core and a capsule wall; wherein, in the capsule core, *Paecilomyces lilacinus* spore powder, a vegetable oil, glucose, peptone, a cellulose nanofiber, sodium citrate, and a surfactant are combined to form an emulsifiable capsule core; and in the capsule wall, chitosan, gelatin, polyvinyl alcohol, glycerol, and water are combined to form a water-responsive shell. The environmentally responsive *Paecilomyces lilacinus* microbeads can stimulate the dissolution of polyvinyl alcohol in the shell according to the moisture content in the soil, so that the water in the soil flows into the microbeads. The cellulose nanofibers in the microbeads absorb water and expand, blocking the holes in the shell, resulting in the inability of spores to flow out.

13 Claims, 1 Drawing Sheet

ENVIRONMENTALLY RESPONSIVE *PAECILOMYCES LILACINUS* MICROBEAD AND PREPARATION METHOD THEREOF

CROSS REFERENCE TO THE RELATED APPLICATIONS

This application is based upon and claims priority to Chinese Patent Application No. 202011029908.7, filed on Sep. 27, 2020, the entire contents of which are incorporated herein by reference.

TECHNICAL FIELD

The invention relates to an environmentally responsive *Paecilomyces lilacinus* microbead and its preparation method and application, belonging to the technical field of agricultural microorganism.

BACKGROUND

*Paecilomyces lilacinus* (*P. lilacinus*) is an effective egg-parasitic fungus of plant phytopathogenic nematodes in the deuteromycotina, hyphomycetes, and *paecilomyces*. More than 50 species have been found, all of which belong to insect pathogens or nematode pathogens. The study shows that *Paecilomyces lilacinus* can not only promote the growth of a variety of plants, but also prevent and control many plant diseases, and it has many advantages including safety, no pollution, high efficiency, and wide host range.

In recent years, climate change worsens, and continuous large-scale rainfall occurs in some areas, resulting in the phenomenon of precipitation increase and decrease in different regions and periods, rain and high humidity. This has a significant impact on the period growth and decline of crop diseases and insect pests and disasters in regions. At present, there are three main types of biofertilizers: liquid, powder and granules. These types of biofertilizers can only have a short time effect in farmland. Most of the strains continue to inactivate or lose with the growth of storage time, resulting in fewer strains that finally reach the roots of crops. As a result, they cannot improve the growth environment of crops and effectively inhibit the growth of pathogenic microorganisms.

SUMMARY

The present disclosure provides an environmentally responsive *Paecilomyces lilacinus* microbead, which can overcome the shortcomings of the existing technologies. The present disclosure provides an environmentally responsive *Paecilomyces lilacinus* microbead, which first combine polyvinyl alcohol (PVA) and cellulose nanofibers in the microbeads. The microbeads in the invention can stimulate the dissolution of polyvinyl alcohol in the shell according to the moisture content in the soil, so that the water in the soil flows into the microbead. The cellulose nanofibers in the microbeads absorb water and expand, blocking the holes in the shell, resulting in the inability of spores to flow out. Spores germinate and propagate with the help of water and the nutrients in the microbeads. In the process of spores propagation, the protease and chitinase secreted by *Paecilomyces lilacinus* can degrade gelatin and chitosan in the shell, and the release effect can be achieved after a certain time. In high-rainfall areas, or in irrigated soil, the microbeads can increase the number of strains released and improve the fertilizer utilization efficiency.

The present disclosure provides an environmentally responsive *Paecilomyces lilacinus* microbead, the microbead includes a capsule core and a capsule wall; in the capsule core, *Paecilomyces lilacinus* spore powder, vegetable oil, glucose, peptone, cellulose nanofiber, sodium citrate, and surfactant were added to form an emulsifiable concentrate (EC) type capsule core; and in the capsule wall, chitosan, gelatin, polyvinyl alcohol, glycerol, and water were added to form a water-responsive shell.

Further, the compositions of each component in the raw material of the capsule core are as follows (by weight): 20 to 30 portions of *Paecilomyces lilacinus* spore powder, 40 to 60 portions of vegetable oil, 2 to 3 portions of sodium citrate, 1 to 1.5 portions of surfactant, 1 to 1.5 portions of glucose, 0.5 to 1 portions of peptone, and 3 to 5 portions of cellulose nanofibers.

Further, the compositions of each component in the raw material of the capsule wall are as follows (by weight): 1.5 to 2 portions of chitosan, 8 to 10 portions of gelatin, 3 to 5 portions of polyvinyl alcohol, 6 to 10 portions of glycerol, and 60 to 100 portions of water.

Further, the degree of polymerization of the polyvinyl alcohol is 500 to 600.

The invention also offers a preparation method for the environmentally responsive *Paecilomyces lilacinus* microbeads, as follows:

(1) Preparation of core material solution: The *Paecilomyces lilacinus* spore powder, vegetable oil and sodium citrate were mixed evenly in proportion, and then the surfactant was added in proportion to form EC, and followed by glucose, peptone and cellulose nanofibers to obtain the core material solution.

Further, the vegetable oil is corn oil, soybean oil or rapeseed oil.

Further, the surfactant is an anionic emulsifier or a nonionic emulsifier.

Further, the surfactant is a mixture of alkylphenol polyoxyethylene ether, aliphatic alcohol polyoxyethylene ether and sodium lauryl sulfate with a mass ratio of 2:2:1.

(2) Preparation of wall material solution: Chitosan, gelatin, polyvinyl alcohol, glycerol and water were heated and mixed in a proportion of 95-100° C., and kept at 95-96° C. to obtain wall material solution. Primary microbeads are obtained.

(3) Inject the core material and wall material solution obtained in step (1) and (2) into the dripping pill machine respectively, adjust the dripping speed to control the ratio of the two, and drip them into the condensate liquid paraffin.

Further, the dripping speed is 30-60 ml/min, and the inner and outer diameters of the drip tube orifice are 1-8.0 mm and 1.5-8.5 mm.

Further, the ratio of core to wall in step (3) is 4-5:2-3.

(4) Remove the condensate on the surface of the primary microbeads obtained in step (3), then dry in a drum at a constant temperature of 20-30° C. and a constant humidity of 30%-40% to obtain *Paecilomyces* lilacinum microbeads.

Further, after drying, the core material and the wall material weights 85 percent and 15 percent of the microbead mass, respectively.

Beneficial Effects

1. The inventors of the invention first combine polyvinyl alcohol (PVA) and cellulose nanofibers in the microbeads. The polyvinyl alcohol is applied into the microbead shell to prepare an environmentally responsive shell; cellulose nanofiber is applied with *Paecilomyces lilacinus* spore powder to formed an EC (emulsifiable concentrate)—type oil phase, and nutrients such as glucose are added in the core, to embed *Paecilomyces lilacinus* spore powder. Thus, an environmentally responsive *Paecilomyces lilacinus* microbead is obtained, can reduce the contact between the strain and oxygen, avoid the early recovery of the strain, and protect the strain activity to the greatest extent during storage and transportation.

2. For the water-responsive *Paecilomyces lilacinus* microbeads, in the soil with more water content (after irrigation or rainfall), polyvinyl alcohol was dissolved in water, so that the water enters the microbeads and promotes the germination and propagation of spores, and proteases and chitinases secrete and disintegrate the shell from the inside of the microbeads, achieving the purposes of slow release, continuous release, and increased number of released species.

3. For the water-responsive *Paecilomyces lilacinus* microbeads, Cellulose nanofibers in the microbead core can absorb water and adhere to the wall, prevent the leakage of *Paecilomyces lilacinus* spores embedded in EC, fix the growth and propagation of *Paecilomyces lilacinus* in the microbead, thus avoiding the adverse effect of the external environment on the strain, and protecting the strain activity.

4. The invention adopts sodium citrate cross-linked gelatin and chitosan to increase the gel strength, protect microbeads from the effect of external adverse factors during transportation and storage, and improve their storage stability.

5. The invention utilizes proteases and chitinases secreted by strains during the growth and propagation in the microbeads to degrade the shell, so as to achieve the purpose of release; the requirement of high bacterial activity release can be achieved only a small amount of nucleated strains in the microbeads are required, thus reducing the production cost.

DETAILED DESCRIPTION OF THE EMBODIMENTS

In order to make the purpose, technical solution and advantages of this patent clearer, the following is a further detailed description of this patent in combination with the particular embodiment. It is understood that the particular embodiments described herein are solely for the purpose of interpreting the patent and are not intended to limit the invention.

Figure 1:
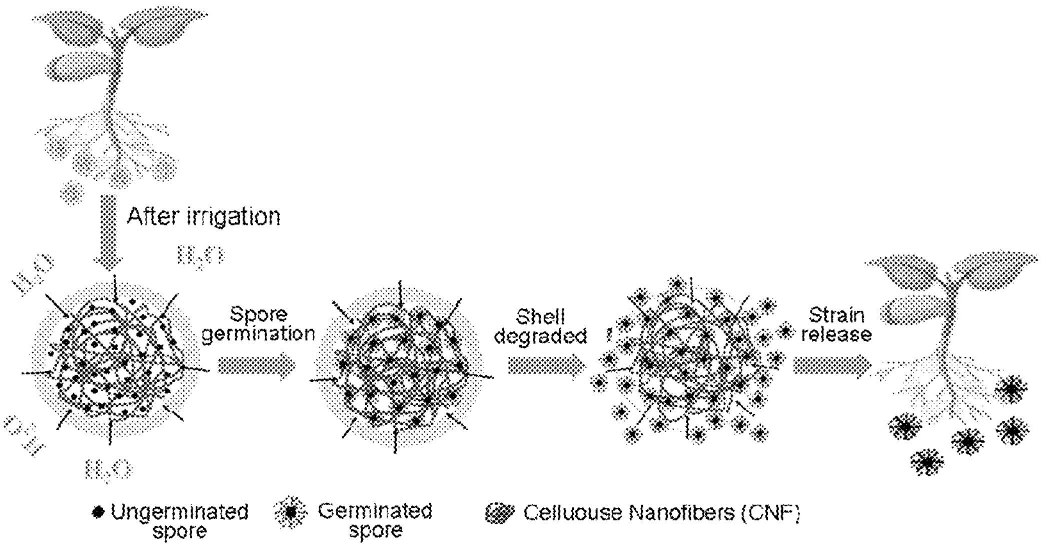
FIG. 1: Schematic diagram of structure and function for the product of the invention.
Figure 2:
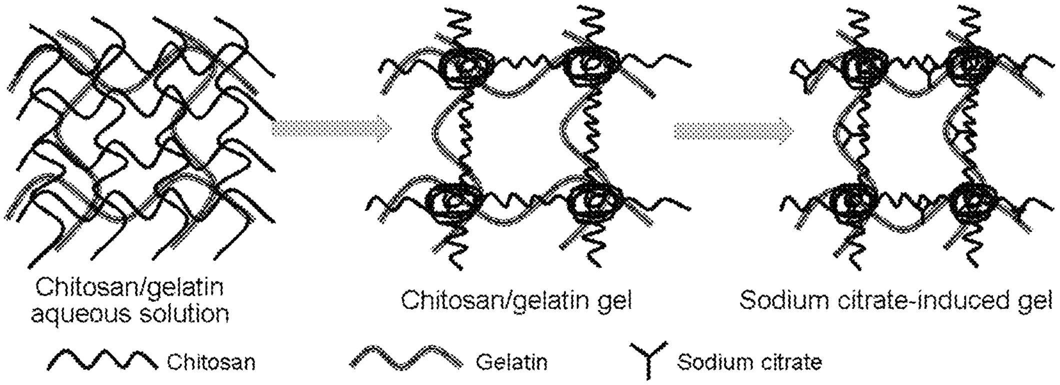
FIG. 2: Schematic diagram of sodium citrate cross-linked chitosan and gelatin in the product of the invention.

The structure of the environmentally responsive microbead is shown in FIG. 1 and FIG. 2, and the following is further explained in combination with specific embodiments.

Embodiment 1: A Water-Responsive *Paecilomyces lilacinus* Microbead (1) Preparation of core material solution: 250 g of *Paecilomyces lilacinus* spore powder, 600 g of corn oil, and 20 g of sodium citrate were added into a beaker and stirred at room temperature for 30 min to mix well, followed by 10 g of the mixture of surfactants dodecylphenol polyoxyethylene ether, polyoxyethylene lauryl ether, and sodium lauryl sulfate (mass ratio 2:2:1); after the formation of EC, 15 g of glucose, 10 g of peptone, and 40 g of cellulose nanofibers were successively added and stirred at room temperature for 30 min to obtain the core material solution.

(2) Preparation of wall material solution: 1.5 g of chitosan, 10 g of gelatin, 4 g of polyvinyl alcohol (the degree of polymerization of polyvinyl alcohol is 500-600), and 8 g of glycerol were added to 80 mL of distilled water, heated to 95-100° C., mixed well, and kept at 95-96° C. to obtain the wall material solution.

(3) Inject the core material and wall material solution obtained in step (1) and (2) into the dripping pill machine, respectively; the dripping speed of the capsule core and the capsule wall is 40 ml/min and 30 ml/min respectively; drip into the condensate liquid paraffin, remove the condensate on the microbead surface, dry in a 35% constant humidity roller at constant temperature 25° C. to obtain the water-responsive *Paecilomyces lilacinus* microbeads with core material and wall material accounting for 85% and 15% of microbead mass, respectively.

Comparative Example 1: A Water-Responsive *Paecilomyces lilacinus* Microbead (Cellulose Nanofiber Deletion Set (1) Preparation of core material solution: 250 g of *Paecilomyces lilacinus* spore powder, 600 g of corn oil, and 20 g of sodium citrate were added into a beaker and stirred at room temperature for 30 min to mix well, followed by 10 g of a mixture of surfactants dodecylphenol polyoxyethylene ether, polyoxyethylene lauryl ether, and sodium lauryl sulfate (mass ratio 2:2:1); after the formation of EC, 15 g of glucose and 10 g of peptone were successively added and stirred at room temperature for 30 min to obtain the core material solution.

(2) Preparation of wall material solution: 1.5 g of chitosan, 10 g of gelatin, 4 g of polyvinyl alcohol (the degree of polymerization of polyvinyl alcohol is 500-600), and 8 g of glycerol were added to 80 mL of distilled water, heated to 95-100° C., mixed well, and kept at 95-96° C. to obtain the wall material solution.

(3) Inject the core material and wall material solution obtained in step (1) and (2) into the dripping pill machine, respectively; the dripping speed of the capsule core and the capsule wall is 40 ml/min and 30 ml/min respectively; drip into the condensate liquid paraffin, remove the condensate on the microbead surface, dry in 35% constant humidity roller at a constant temperature 25° C. to obtain the water-responsive *Paecilomyces lilacinus* microbeads with core material and wall material accounting for 85% and 15% of microbead mass, respectively.

Comparative Example 2: A Water-Responsive *Paecilomyces lilacinus* Microbead (Polyvinyl Alcohol Missing Set (1) Preparation of core material solution: 250 g of *Paecilomyces lilacinus* spore powder, 600 g of corn oil, and 20 g of sodium citrate were added into a beaker and stirred at room temperature for 30 min to mix well, followed by 10 g of a mixture of surfactants dodecylphenol polyoxyethylene ether, polyoxyethylene lauryl ether, and sodium lauryl sulfate (mass ratio 2:2:1); after the formation of EC, 15 g of glucose, 10 g of peptone, and 40 g of cellulose nanofibers were successively added and stirred at room temperature for 30 min to obtain the core material solution.

(2) Preparation of wall material solution: 1.5 g of chitosan, 10 g of gelatin, and 8 g of glycerol were added to 80 mL of distilled water, heated to 95-100° C., mixed well, and kept at 95-96° C. to obtain wall material solution.

(3) Inject the core material and wall material solution obtained in step (1) and (2) into the dripping pill machine, respectively; the dripping speed of the capsule core and the capsule wall is 40 ml/min and 30 ml/min respectively; drip into the condensate liquid paraffin, remove the condensate on the microbead surface, dry in a 35% constant humidity roller at a constant temperature 25° C. to obtain 85% and 15% of microbead mass for core material and wall material, respectively.

Comparative Example 3: A Water-Responsive *Paecilomyces lilacinus* Microbead (Surfactant Missing Set (1) Preparation of core material solution: 250 g of *Paecilomyces lilacinus* spore powder, 600 g of corn oil, and 20 g of sodium citrate were added into a beaker and stirred at room temperature for 30 min and mixed well, followed by 15 g of glucose, 10 g of peptone, and 40 g of cellulose nanofibers successively and stirred at room temperature for 30 min to obtain the core material solution.

(2) Preparation of wall material solution: 1.5 g of chitosan, 10 g of gelatin, 4 g of polyvinyl alcohol (the degree of polymerization of polyvinyl alcohol is 500-600), and 8 g of glycerol were added to 80 mL of distilled water, heated to 95-100° C., mixed well, and kept at 95-96° C. to obtain the wall material solution.

(3) Inject the core material and wall material solution obtained in step (1) and (2) into the dripping pill machine, respectively; the dripping speed of the capsule core and the capsule wall is 40 ml/min and 30 ml/min respectively; drip into the condensate liquid paraffin, remove the condensate on the microbead surface, dry in 35% constant humidity roller at a constant temperature 25° C. to obtain 85% and 15% of microbead mass for core material and wall material, respectively.

Case Effect Test:

(1) Microbead Change and Viable Bacteria Release in Water Environment

Take 30 g of microbeads prepared in Embodiment 1 and Comparative Examples 1-3, divide them into three portions, place them in a culture dish containing a small amount of sterile water, place them at 28° C. for 5 days, observe the changes in the internal and external structure of microbeads every day, and determine the number of bacterial strains in the microbeads, the result is Table 1.

TABLE 1

| | | Internal variation | External variation | Strain number in microbeads (cfu/g) |
|---|---|---|---|---|
| Dayl | Embodiment 1 | Moisture increased | Small amount of water adsorption on microbead shell | $2.4 \times 10^7$ |
| | Comparative Example 1 | Moisture increased | Small amount of water adsorption on microbead shell | $2.2 \times 10^6$ |
| | Comparative Example 2 | No significant change | No significant change | $2.4 \times 10^7$ |
| | Comparative Example 3 | Moisture increased | Small amount of water adsorption on microbead shell | $2.3 \times 10^7$ |
| Day2 | Embodiment 1 | Moisture increased | Small amount of water adsorption on microbead shell | $5.6 \times 10^7$ |
| | Comparative Example 1 | EC reduced | Small amount of water adsorption on microbead shell | $4.4 \times 10^5$ |
| | Comparative Example 2 | No significant change | No significant change | $2.6 \times 10^7$ |
| | Comparative Example 3 | Moisture increased | Small amount of water Adsorption on microbead shell | $2.2 \times 10^7$ |
| Day3 | Embodiment 1 | Moisture increased, trace hyphal growth | Small amount of water adsorption on microbead shell | $6.5 \times 10^8$ |
| | Comparative Example 1 | Small amount of hyphal growth with reduced EC | Small amount of water adsorption on microbead shell | $3.3 \times 10^3$ |
| | Comparative Example 2 | No significant change | No significant change | $2.1 \times 10^7$ |
| | Comparative Example 3 | Moisture increased, no hyphal growth | Small amount of water adsorption on microbead shell | $2.3 \times 10^7$ |
| Day4 | Embodiment 1 | Moisture increased, heavy hyphal growth | A small amount of hyphal in the microbead shell and thinning of the shell layer | $1.4 \times 10^9$ |
| | Comparative Example 1 | Small amount of hyphal growth with reduced EC | Small amount of water adsorption on microbead shell | $5.8 \times 10^2$ |

TABLE 1-continued

| | | Internal variation | External variation | Strain number in microbeads (cfu/g) |
|---|---|---|---|---|
| | Comparative Example 2 | No significant change | No significant change | $2.3 \times 10^7$ |
| | Comparative Example 3 | Moisture increased, no hyphal growth | Small amount of water adsorption on microbead shell | $2.3 \times 10^7$ |
| Day5 | Embodiment 1 | Moisture increased, heavy hyphal growth | Small amount of hyphal in microbead shell, shell layer breaks | $4.8 \times 10^9$ |
| | Comparative Example 1 | Extensive hyphal growth with reduced EC | Small amount of water adsorption on microbead shell | $4.4 \times 10^2$ |
| | Comparative Example 2 | No significant change | No significant change | $2.5 \times 10^7$ |
| | Comparative Example 3 | Moisture increased, no hyphal growth | Small amount of water adsorption on microbead shell | $2.1 \times 10^7$ |

The test results are shown in Table 1, and the environmentally responsive *Paecilomyces lilacinus* microbeads prepared according to the method described in Embodiment 1 can adjust the release rate and amount of entrapped viable bacteria according to the moisture content. When polyvinyl alcohol is added into the shell, the polyvinyl alcohol in the shell is dissolved due to the water in the microbead shell, so that the external water enters the microbead and promotes the germination of bacteria cell. When there is no polyvinyl alcohol in the shell but a small amount of moisture, the external moisture cannot enter the microbeads. When cellulose nanofibers are added to the core material, cellulose nanofibers absorb water and adhere to the wall, so that the internal EC encapsulated strains cannot leak, and the strains grow and propagate inside, so as to achieve the effect of slow release. When the EC core is used (vegetable oil and surfactant were added at the same time), the strain can grow and propagate normally. When the capsule core is only a non-EC phase, the strain is wrapped inside the oil phase and cannot contact the external environment for the time being, so it cannot propagate normally for the time being, resulting in that the strain cannot function in a short time.

(2) Effect of Storage Time on Strain Viability:

The samples prepared in Embodiment 1 and Comparative Examples 1-3 were sealed and stored at room temperature for 0-180 days. After storage, take 15 g of the sample, dilute it in 100 g of normal saline, add 0.5 wt % Tween 80, and place it in a conical flask. Shake it with glass microbeads (spread flat at the bottom) in a shaker (200 rpm) for 45 min. Then, the strains were diluted with normal saline according to the activity and number of strains. The dilutions were spread on Rose Bengal medium, incubated in a 28° C. incubator for 48 h, and counted. As shown in Table 2, the results showed that the strain activity of the product prepared in Embodiment 1 remained well during storage, indicating that the microbeads prepared by this method could better protect the bacteria cell during storage. For the product prepared with Comparative Example 3, there will be trace loss during storage, due to the use of non-EC type oil-phase as the core for Comparative Example 3, there will be loss in the presence of non-EC type oil-phase in the spores.

TABLE 2

| Storage Time (days) | Embodiment 1 (cfu/g) | Comparative Example 1 (cfu/g) | Comparative Example 2 (cfu/g) | Comparative Example 3 (cfu/g) |
|---|---|---|---|---|
| 0 | $2.4 \times 10^7$ | $2.5 \times 10^7$ | $2.3 \times 10^7$ | $2.1 \times 10^7$ |
| 30 | $2.2 \times 10^7$ | $1.7 \times 10^7$ | $2.1 \times 10^7$ | $1.5 \times 10^7$ |
| 60 | $2.1 \times 10^7$ | $1.5 \times 10^7$ | $1.5 \times 10^7$ | $1.3 \times 10^7$ |
| 90 | $1.9 \times 10^7$ | $1.4 \times 10^7$ | $1.2 \times 10^7$ | $1.1 \times 10^7$ |
| 120 | $1.8 \times 10^7$ | $1.3 \times 10^7$ | $1.1 \times 10^7$ | $9.8 \times 10^6$ |
| 180 | $1.5 \times 10^7$ | $1.1 \times 10^7$ | $1 \times 10^7$ | $9.6 \times 10^6$ |

(3) Field Tests

Fertilizer efficacy tests were conducted on the control effect of root-knot nematodes, and data collection and analysis were performed on the test samples. A total of four treatments (Treatment I: Embodiment 1; Treatment II: Comparative Example 1; Treatment III: Comparative Example 2; Treatment IV: Comparative Example 3) and an untreated control were designed in the experiment. The plants tested are cucumbers. Before transplanting, 5 g of prepared samples were added to each soil pit, and other cultivation measures were uniformly and normally operated to ensure a consistent plant growth environment. After 30 days of colonization, the yield was counted, and at the late harvest stage, the roots were excavated to investigate the root knot index and evaluate the control effect. The control effect is shown in Table 3, and obviously Embodiment 1 can effectively control root-knot nematodes and improve cucumber yield.

Grading criteria for root-knot nematodes:

Grade 0: Healthy roots, no root knots

Grade 1; few root knots, "root knot %"<25%

Grade 2: Moderate number of root-knots, "root knot %"≈25%-50%

Grade 3: High number of root-knots, "root knot %"≈50%-75%

Grade 4: Too many root-knots, "root knot %">75%

Root-knot index=Σ(each grade of disease index× Corresponding number of diseased strain/Investigated strain number)×100%

Prevention and control effect=(1−Root-knot index in treatment area/Root-knot index in control area)×100%

TABLE 3

| | Root-knot index | Prevention and control effect (%) | Yield increase (%) |
|---|---|---|---|
| Treatment I | 19 | 75.64 | 25.6 |
| Treatment II | 38 | 51.28 | 16.8 |
| Treatment III | 53 | 32.05 | 6.9 |
| Treatment IV | 41 | 47.43 | 10.4 |
| Control | 78 | — | — |

Embodiment 2: A Water-Responsive *Paecilomyces lilacinus* Microbead (1) Preparation of core material solution: 200 g of *Paecilomyces lilacinus* spore powder, 400 g of soybean oil, and 25 g of sodium citrate were added into a beaker and stirred at room temperature for 30 min to mix well, followed by 12 g of a mixture of surfactant octylphenol polyoxyethylene ether and sodium alkyl sulfate (mass ratio 2:1); after the formation of EC, 10 g of glucose, 5 g of peptone, and 30 g of cellulose nanofibers were successively added and stirred at room temperature for 30 min to obtain the core material solution.

(2) Preparation of wall material solution: 1.5 g of chitosan, 8 g of gelatin, 3 g of polyvinyl alcohol (the degree of polymerization of polyvinyl alcohol is 500-600), and 6 g of glycerol were added to 60 mL of distilled water, heated to 95-100° C., mixed well, and kept at 95-96° C. to obtain the wall material solution.

(3) Inject the core material and wall material solution obtained in step (1) and (2) into the dripping pill machine, respectively; the dripping speed of capsule core is 40 ml/min, the dripping speed of capsule wall is 20 ml/min; drip into the condensate liquid paraffin, remove the condensate on the microbead surface, dry in a 35% constant humidity roller at constant temperature 25° C. to obtain the water-responsive *Paecilomyces lilacinus* microbeads with core material and wall material accounting for 80% and 20% of microbead mass, respectively.

Embodiment 3: A Water-Responsive *Paecilomyces lilacinus* Microbead (1) Preparation of core solution: 300 g of *Paecilomyces lilacinus* spore powder, 500 g of rapeseed oil, and 30 g of sodium citrate were added to a beaker and stirred at room temperature for 30 min to mix well, followed by 12 g of a mixture of surfactants castor oil polyoxyethylene ether, styrenyl phenol polyoxyethylene ether, and calcium dodecyl benzene sulfonate (mass ratio 3:1:1); after the formation of EC, 12 g of glucose, 8 g of peptone, and 50 g of cellulose nanofibers were successively added and stirred at room temperature for 30 min to obtain the core solution.

(2) Preparation of wall material solution: 2.0 g of chitosan, 10 g of gelatin, 5 g of polyvinyl alcohol (the degree of polymerization of polyvinyl alcohol is 500-600), and 10 g of glycerol were added to 100 mL of distilled water, heated to 95-100° C., mixed well, and kept at 95-96° C. to obtain the wall material solution.

(3) Inject the core material and wall material solution obtained in step (1) and (2) into the dripping pill machine, respectively; the dripping speed of capsule core is 50 ml/min, the dripping speed of capsule wall is 30 ml/min; drip into the condensate liquid paraffin, remove the condensate on the microbead surface, dry in a 35% constant humidity roller at constant temperature 25° C. to obtain the water-responsive *Paecilomyces lilacinus* microbeads with core material and wall material accounting for 90% and 10% of microbead mass, respectively.

The embodiments above represent only a few embodiments of the invention, the detailed and specific description of which cannot be construed as a limitation of the scope of the patent. It should be noted that, for the general technicians in this field, without separating from the conception of this patent, the aforesaid modes of execution can also make several deformations, combinations and improvements, which are all within the scope of protection of this patent. Therefore, the scope of protection of this patent shall be subject to the claims.

What is claimed is:

1. An environmentally responsive *Paecilomyces lilacinus* microbead, comprising a capsule core and a capsule wall; wherein, in the capsule core, *Paecilomyces lilacinus* spore powder, a vegetable oil, glucose, peptone, a cellulose nanofiber, sodium citrate, and a surfactant are combined to form an emulsifiable capsule core; and in the capsule wall, chitosan, gelatin, polyvinyl alcohol, glycerol, and water are combined to form a water-responsive shell.

2. The environmentally responsive *Paecilomyces Lilacinus* microbead of claim 1, wherein parts by weight of compositions of the capsule core are as follows: 20 to 30 parts of the *Paecilomyces Lilacinus* spore powder, 40 to 60 parts of the vegetable oil, 2 to 3 parts of the sodium citrate, 1 to 1.5 parts of the surfactant, 1 to 1.5 parts of the glucose, 0.5 to 1 part of the peptone, and 3 to 5 parts of the cellulose nanofiber.

3. The environmentally responsive *Paecilomyces Lilacinus* microbead of claim 1, wherein parts by weight of compositions of the capsule wall are as follows: 1.5 to 2 parts of the chitosan, 8 to 10 parts of the gelatin, 3 to 5 parts of the polyvinyl alcohol, 6 to 10 parts of the glycerol, and 60 to 100 parts of the water.

4. The environmentally responsive *Paecilomyces Lilacinus* microbead of claim 1, wherein a mass ratio of the capsule core to the capsule wall is (4-5):(2-3).

5. The environmentally responsive *Paecilomyces Lilacinus* microbead of claim 1, wherein the vegetable oil is one selected from the group consisting of corn oil, soybean oil and grapeseed oil.

6. The environmentally responsive *Paecilomyces Lilacinus* microbead of claim 1, wherein the surfactant is an anionic emulsifier or a nonionic emulsifier.

7. The environmentally responsive *Paecilomyces Lilacinus* microbead of claim 1, wherein the surfactant is a mixture of alkylphenol polyoxyethylene ether, fatty alcohol polyoxyethylene ether and sodium lauryl sulfate, and a mass ratio of the alkylphenol polyoxyethylene ether, the fatty alcohol polyoxyethylene ether and the sodium lauryl sulfate is 2:2:1.

8. A preparation method of the environmentally responsive *Paecilomyces Lilacinus* microbead of claim 1, comprising the following steps:

(1) preparation of a core material solution: adding and mixing the *Paecilomyces lilacinus* spore powder, the vegetable oil and the sodium citrate to obtain a first mixture, and then adding the surfactant into the first mixture to form an emulsifiable concentrate, and then adding the glucose, the peptone and the cellulose nanofiber into the emulsifiable concentrate to obtain the core material solution;

(2) preparation of a wall material solution: mixing and heating the chitosan, the gelatin, the polyvinyl alcohol, the glycerol and the water at 95-100° C. to obtain a second mixture, and performing a heat preservation on the second mixture at 95-96° C. to obtain the wall material solution;

(3) injecting the core material solution and the wall material solution obtained in step (1) and (2) into a dripping pill machine respectively, adjusting a dripping speed to control a ratio of the core material solution and the wall material solution, and dripping the core material solution and the wall material solution into liquid paraffin to obtain a primary microbead;

(4) removing the liquid paraffin on a surface of the primary microbead obtained in step (3) to obtain a treated primary microbead, and performing a drying treatment on the treated primary microbead in a roller under a constant temperature and constant humidity to obtain the environmentally responsive *Paecilomyces lilacinus* microbead.

9. The preparation method of claim 8, wherein the vegetable oil is one selected from the group consisting of corn oil, soybean oil and rapeseed oil.

10. The preparation method of claim 8, wherein the surfactant is an anionic emulsifier or a nonionic emulsifier.

11. The preparation method of claim 10, wherein the surfactant is a mixture of alkylphenol polyoxyethylene ether, fatty alcohol polyoxyethylene ether and sodium lauryl sulfate, and a mass ratio of the alkylphenol polyoxyethylene ether, the fatty alcohol polyoxyethylene ether and the sodium lauryl sulfate is 2:2:1.

12. The preparation method of claim 8, wherein the ratio of the core material solution to the wall material solution in step (3) is (4-5):(2-3).

13. The preparation method of claim 8, wherein after the drying treatment, a mass percent of the capsule core to the environmentally responsive *Paecilomyces lilacinus* microbead is 85% and a mass percent of the capsule wall to the environmentally responsive *Paecilomyces lilacinus* microbead is 15%.

* * * * *